United States Patent [19]

Hellstrom et al.

[11] Patent Number: 4,766,315

[45] Date of Patent: Aug. 23, 1988

[54] APPARATUS AND PROCESS FOR MEASURING PHYSICAL PARAMETERS OF SHEET MATERIAL

[75] Inventors: Ake A. Hellstrom, Columbus; James E. Throm, Jr., Galloway, both of Ohio

[73] Assignee: AccuRay Corporation, Columbus, Ohio

[21] Appl. No.: 885,017

[22] Filed: Jul. 14, 1986

[51] Int. Cl.$^4$ .................. G01N 21/35; G01N 21/86
[52] U.S. Cl. ........................ 250/339; 250/341; 250/349
[58] Field of Search ............ 250/339, 370 L, 338 FE, 250/338 PY, 338 SE, 341, 349, 350, 352

[56] References Cited

U.S. PATENT DOCUMENTS

| | | | |
|---|---|---|---|
| 3,228,282 | 1/1966 | Barker, Jr. ..................... | 356/429 |
| 3,405,268 | 10/1968 | Brunton ........................ | 250/339 |
| 3,793,524 | 2/1974 | Howarth ....................... | 250/339 |
| 4,052,615 | 10/1977 | Cho ............................... | 250/341 |
| 4,230,945 | 10/1980 | Meir et al. .................... | 250/370 L |
| 4,300,049 | 11/1981 | Sturm ........................... | 250/339 |
| 4,306,151 | 12/1981 | Chase ........................... | 250/341 |
| 4,490,612 | 12/1984 | Törmälä ....................... | 250/339 |
| 4,560,875 | 12/1985 | Crowder ....................... | 250/343 |
| 4,577,104 | 3/1986 | Sturm ........................... | 250/339 |
| 4,582,520 | 4/1986 | Sturm ........................... | 65/3.43 |

Primary Examiner—Janice A. Howell
Assistant Examiner—Constantine Hannaher
Attorney, Agent, or Firm—Joseph R. Black

[57] ABSTRACT

An apparatus and process for measuring physical parameters of sheet material via infrared absorption phenomena is disclosed. The invention employs an integral filter-detector package comprising at least two optical filter-detector combinations. The package is contained within a conventional sensor housing which traverses back and forth across the sheet material. The package may comprise an additional filter-detector combination that is selected to produce a detector response having a significantly higher signal-to-noise ratio than the response of remaining detectors. The former response is used in combination with synchronous detectors to provide a reference of the general shape and phase of the latter responses in the absence of high noise.

26 Claims, 3 Drawing Sheets

APPARATUS AND PROCESS FOR MEASURING PHYSICAL PARAMETERS OF SHEET MATERIAL

BACKGROUND OF THE INVENTION

1. Technical Field of the Invention

This invention relates to apparatus and processes for measuring physical parameters of sheet material by directing electromagnetic radiation from a source to the material and electronically processing infrared detector responses associated with selected wavelengths of radiation which passes through or otherwise interacts with the material.

2. Description of Prior Art

Measurement of physical parameters of sheet material through the use of infrared absorption phenomena is well-known. Typical procedures employ a source of electromagnetic radiation having a spectral output that includes the infrared region, a collimator or other arrangement for directing the radiation toward the sheet material, a chopper for modulating the directed radiation, filters for passing selected bands of radiation, one or more infrared detectors that produce responses which depend on the intensity of radiation passing through the filters, and electronic processing means for deriving the measurement from the detector responses. The filters may be mounted in a rotating chopper so that radiation transmissions are time-multiplexed to a single detector as in U.S. Pat. Nos. 4,052,615 Cho, or to separate, plural detectors as in 4,300,049 Sturm. Alternatively, the procedure may employ plural sources with two or more detectors as in U.S. Pat. No. 4,306,151 Chase, or a single source with a beam splitter and plural, separate detectors as in U.S. Pat. No. 3,405,268 Brunton.

The physical parameter in question is measured by taking advantage of the selective absorption of certain wavelengths of infrared radiation by certain constituents of the sheet material as taught, for instance, by U.S. Pat. No. 3,228,282 Barker. The typically heterogeneous nature of the sheet material introduces sources of measurement error, some of which can be compensated for by measuring the absorption for two or more different bands of radiation and interrelating the measurements to produce corrected measurements indicative of the physical parameter or parameters in question. This technique is exemplified in U.S. Pat. Nos. 3,405,268 Brunton and 4,577,104 Sturm.

Other sources of measurement error are compensated for by the geometric arrangement of the apparatus, as illustrated in U.S. Pat. Nos. 3,793,524 Howarth and 4,052,615 Cho.

Additional sources of error inhere in the methods by which certain components of such previous apparatus have been used. Specifically, those which use mobile filters to produce sequential detector responses in a time-multiplex arrangement may introduce sources of error as explained in U.S. Pat. No. 4,300,049 Sturm (cols. 3–4). In those which employ plural, separate detectors, the detectors are disposed on separate substrates and may be separately cooled. Either of these conditions may affect the relative thermal stability of the detectors and represent yet another source of error. Moreover, when plural detectors are used in conjunction with a beam splitter, the radiation emitted from the source is divided among the detectors, thereby yielding weaker detector responses. Where stronger responses are desired, the source intensity may be increased— which increases cooling requirements and decreases longevity for the source— or the weak responses may be further amplified, which yields no improvement in signal-to-noise ratio and heightens electronic filtering requirements in conventional signal processing circuits.

SUMMARY OF THE INVENTION

This invention provides apparatus and associated processes for measuring physical parameters of sheet material by directing electromagnetic radiation from a source to the material and electronically processing infrared detector responses associated with selected bands of infrared radiation which passes through or otherwise interacts with the material, comprising a sensor housing, and an integral filter-detector package (hereinafter "integral package") contained within the sensor housing and containing both a plurality of filters which pass selected bands of radiation, and a corresponding plurality of detectors which detect the radiation passed through the filters.

The detectors may be disposed on a common substrate, and the integral package may further contain a thermoelectric cooler to provide internal temperature control.

The integral package may contain a phase-reference detector which detects radiation emitted from the source that is within a selected band. In that event the integral package will also contain at least two additional detectors which detect infrared radiation within two additional bands that may or may not be included within the band detected by the phase-reference detector. Alternatively, the phase-reference detector may be isolated from the integral package. The phase-reference detector and associated circuitry are used to condition detector responses from the remaining detectors in accordance with the response from the phase-reference detector.

The integral package will typically be displaced from the transmission axis of the source. The phase-reference detector may also be displaced from the transmission axis, although typically to a lesser degree than the integral package, and in a preferred embodiment has a location along the transmission axis.

An object of this invention is to provide apparatus and processes for measuring physical parameters of sheet material via infrared absorption phenomena without the need for plural radiation sources, filter wheels, beam splitters, or similar devices and arrangements.

Another object of the invention is to provide such apparatus and processes that eliminate certain sources of measurement error which inhere in the use of two or more separate detectors.

A further object of the invention is to provide in such apparatus and processes a unique and advantageous method for deriving reliable measurements from relatively weak detector responses.

BRIEF DESRIPTION OF THE DRAWINGS

DETAILED DESCRIPTION OF PREFERRED EMBODIMENTS

Although the invention can be incorporated in a variety of sensor designs for measuring properties of sheet material (such as those shown, for example, in U.S. Pat. Nos. 4,306,151 Chase, 3,793,524, Howarth, or 3,405,268 Brunton), it is herein described and illustrated as embodied in a sensor design having a hemispherical detector housing similar to that of U.S. Pat. No. 4,052,615 Cho. The disclosure of the latter patent is hereby incorporated by reference.

The term "sensor housing" as used herein, is intended to encompass both those systems which employ a single-portion housing on one side of the sheet material, and those which employ a two-portion housing with a portion on each side of the sheet material. The context in which the term "filter" (or a form thereof) is used will indicate whether optical or electrical filtering is being described.

Figure 1:
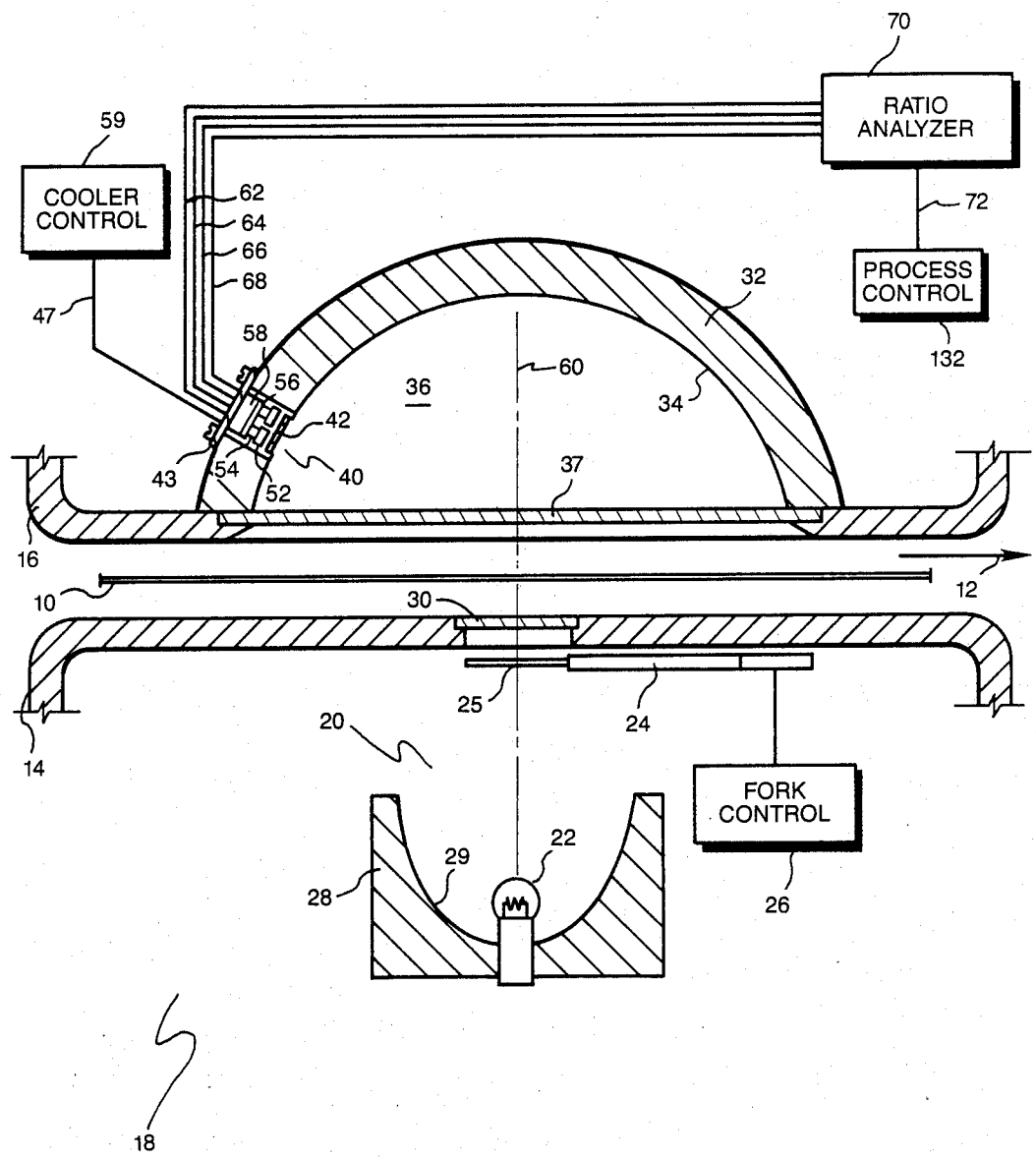
FIG. 1 is a generally schematic, partially sectional view of an embodiment of the invention.

Referring to FIG. 1, the numeral 10 designates sheet material that is typically in motion during production thereof, as indicated at 12. The sheet material 10 is shown passing between the source housing 14 and detector housing 16 of a two-portion sensor housing 18. The sensor housing 18 is typically mounted on a conventional sheet-traversing structure (not shown) and in communication with remote means for controlling those physical parameters of the sheet material 10 which the sensor measures.

A source arrangement, indicated generally as 20, is contained within the source housing 14 and includes a conventional lamp 22 and a chopper 24. The lamp 22 provides a source of electromagnetic radiation over a spectral band that includes the infrared region. The chopper 24 may be a motor-driven rotating disc, an electronically-driven tuning fork, or any device suitable for modulating a radiation beam. A tuning fork is preferred for its stability, low cost, and low heat generation. The chopper 24 is driven by a conventional controller 26 at a desired modulation frequency.

The source arrangement 20 preferably includes an elliptical reflector 28 that is secured by conventional means to the source housing 14. An ellipsoidal region is defined by the reflecting surface 29 of the elliptical reflector 28. The foci of the ellipsoidal region define the nominal locations of the lamp 22 and the modulating portion 25 of the chopper 24. Just above the modulating portion 25 is a first window 30 through which radiation is directed to the sheet 10.

The detector housing 16 contains a hemispherical body 32 having a highly-polished, reflecting surface 34 that forms a hemispherical cavity 36. An integral filter-detector package, generally designated as 40, is attached to the hemispherical body 32 and contains means for detecting radiation emitted from the source 20 and passing through, or otherwise interacting with the sheet material 10. The integral package 40 and the reflecting surface 34 are protected by a second window 37 placed between the detector housing 16 and the hemispherical body 32.

Figure 3:
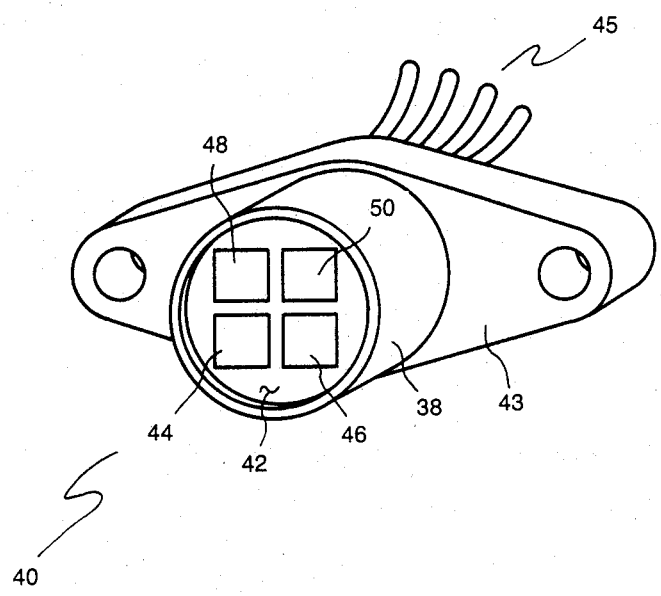
FIG. 3 is a generally perspective, partially schematic illustration of an integral filter-detector package that may be used with the invention.

The integral package 40 is illustrated in FIGS. 1 and 3 and includes a filter-detector housing 38 with an access window 42. A mounting plate 43 is added to secure the integral package 40 to the hemispherical body 32. The numeral 45 generally designates communication lines for detector responses 62, 64, 66, 68, and the number 47 designates a two-way communication line between the integral package 40 and a cooler control unit 59. Radiation entering through the access window 42 into the filter-detector housing 38 is simultaneously filtered and simultaneously detected in a plurality (four are shown) of radiation channels 44, 46, 48, and 50. Each radiation channel—as, for example, that designated by the numeral 50—comprises a filter 52 selected to pass a desired band of radiation, and a corresponding detector 54. The detectors are preferably disposed on a common substrate 56, and the integral package 40 preferably contains a thermoelectric cooler 58 to control its internal temperature and thereby control the temperature of the filters and detectors. These features are individually and collectively important since the performances of both detectors and filters are affected by physical characteristics which are temperature-dependent. The cooler control unit 59 responds to the internal temperature of the integral package 40 as indicated by a thermistor (not shown) contained therein, and controls operation of the thermoelectric cooler 58. Integral packages of the above description may be obtained from IR Industries, Inc., Waltham, Mass.

The number of radiation channels needed in the integral package 40 will vary with the application. For example, four channels are necessary in applications to which the invention of U.S. Pat. No. 4,577,104 Sturm is directed, wherein it is desired to measure radiation intensity for four narrow bands of radiation centered at about $1.83\mu$, $1.93\mu$, $1.89\mu$, and $2.12\mu$. In contrast, three channels are necessary in applications to which U.S. Pat. No. 4,582,520 Sturm is directed (corresponding to IR wavelengths of $1.35\mu$, $1.50\mu$, and $1.75\mu$), and only two are necessary to incorporate the integral package 40 in the invention of U.S. Pat. No. 3,228,282 Barker. One-channel packages are known in the field of sheet material property measurement, as exemplified in U.S. Pat. No. 4,052,615 Cho (col. 5, l. 16–25).

Referring again to FIG. 1, the integral package 40 may be located along the transmission axis 60, or may be displaced from the transmission axis as shown. The degree of displacement may depend on the application or, more particularly, the physical characteristics of the sheet material 10 being examined, as taught in U.S. Pat. Nos. 3,793,524 Howarth and 4,052,615 Cho (col. 5, l. 36–41).

In the operation of the invention as embodied in FIG. 1, electromagnetic radiation emitted from the source 20 and passed through the sheet material 10 and into the hemispherical cavity 36 is optically filtered within radiation channels 44, 46, 48, 50, to pass four selected bands of radiation to four corresponding detectors. The detectors produce detector responses 62, 64, 66, and 68 that are communicated to a conventional ratio analyzer circuit 70, which in turn produces one or more outputs 72, indicative of the measured physical parameter or parameters of the sheet material 10. These outputs 72 may be further processed and delivered to a visual recorder or a process control device 132 through a computer interface (not shown).

In some applications it may be difficult to produce detector responses with suitably high signal-to-noise ratios. This could occur in a variety of circumstances, one of which is the use of a relatively low-intensity source 20 in conjunction with a relatively small integral package 40 having multiple radiation channels. Another aspect of the invention pertains to the use of what is herein termed a "phase-reference detector" to provide reliable measurements in such applications. A phase-reference detector is 35 herein defined as a detector, the response of which is used in conjunction with a synchronous detector (a conventional circuit) to condition weaker infrared detector responses.

Referring again to FIGS. 1 and 3, one radiation channel 50 of the integral package 40 may contain a detector 54 that serves as a phase-reference detector. The filter 52 corresponding to this detector 54 is selected to pass a given band of radiation. The three filters in the remaining radiation channels 44, 46, and 48 pass narrower bands of infrared radiation, all of which may be included within the radiation band passed by the first filter 52. For example, if one desires to measure both the basis weight and moisture content of paper or other absorbent material in a manner similar to that taught by U.S. Pat. No. 3,405,268 Brunton, the three filters in radiation channels 44, 46, and 48 can be selected to pass relatively narrow bands of radiation centered at about 1.95µ, 1.83µ, and 2.12µ, respectively. The filter 52 corresponding to the phase-reference detector 54 can be selected to pass a relatively broad band of radiation extending from about 0.95µ to about 2.6µ. Since the phase-reference detector 54 receives radiation over a much broader range of wavelengths than any other single detector, it will produce a response 62 with a higher signal-to-noise ratio than the responses 64, 66, and 68 from the detectors in radiation channels 44, 46, and 48 respectively. It is not necessary that the band of radiation passed by the filter 52 corresponding to the phase-reference detector 64 encompass those bands of radiation passed by the filters in the remaining radiation channels 44, 46, and 48. What is important is that the filter 52 is selected so that its corresponding detector 54 will produce a response 62 with a significantly higher signal-to-noise ratio than obtains for the responses 64, 66, and 68 from the remaining detectors. By appropriate modification of the ratio analyzer circuit 70, the stronger response 62 from the phase-reference detector 54 can be used to condition the responses 64, 66, and 68 from the remaining detectors and thereby produce more accurate measurements.

Figure 4:
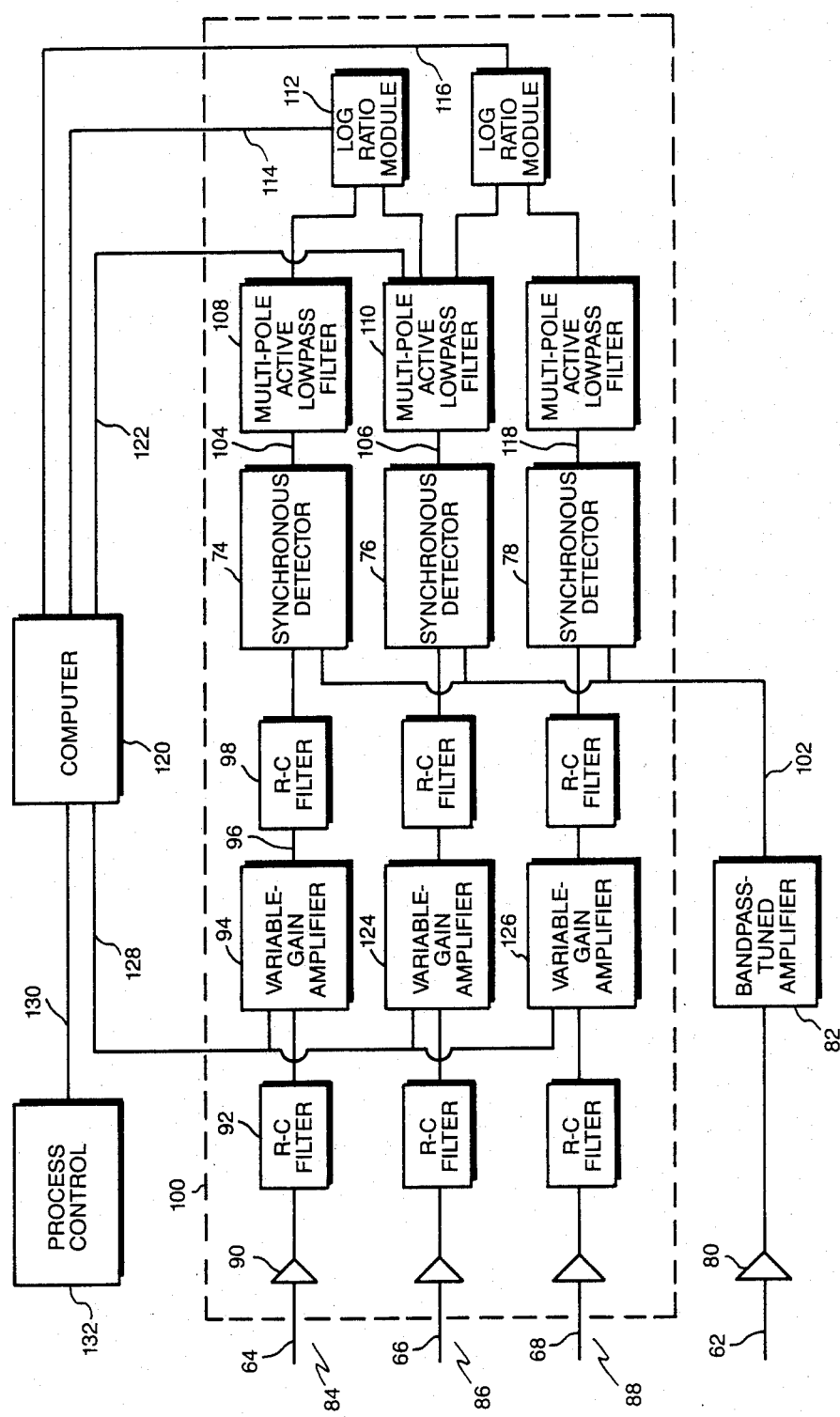
FIG. 4 is a schematic illustration of a modified ratio analyzer circuit that may be used in producing measurements of physical parameters of sheet material in accordance with the invention.

An example of such a circuit is schematically illustrated in FIG. 4 and indicated generally by a rectangularly-shaped box 100 enclosed by dashed lines. Detector responses 64, 66, and 68 are fed into information channels 84, 86, and 88, respectively. In each information channel, as in information channel 84, for example, the detector response 64 is processed through a pre-amp 90 and a filter 92 and fed to a variable-gain amplifier 94. The output of the variable-gain amplifier 94 is an amplified response 96 that is filtered as shown at 98. The response 62 from the phase-reference detector 54 (FIG. 1) is processed through a pre-amp 80 and fed to a bandpass-tuned amplifier 82. The bandpass-tuned amplifier 82 is a conventional amplification and filtering circuit having component specifications that are selected in accordance with the modulation frequency of the chopper 24. The output of the bandpass-tuned amplifier 82 is a reference response 102. The reference response 102 and the amplified response 96 are fed into a synchronous detector 74. The output of the synchronous detector 74 is a conditioned response 104. The conditioned response 104, and a second conditioned response 106 processed from the detector response 66 in another information channel 86, are filtered as indicated at 108 and 110, respectively, and are fed into a log ratio module 112 where they are processed to produce a measurement response 114 indicative of some physical parameter of the sheet material 10. The measurement response 114, and a second measurement response 116 processed from conditioned responses 106 and 118 in information channels 86 and 88, respectively, are inputs to a remote computer 120. An additional input, indicated as 122, is used as part of a feedback loop that includes a gain-setting signal 128 delivered from the computer 120 to all variable-gain amplifiers 94, 124, and 126. The measurement responses 114, 116 may be further processed by the computer 120, which may send an adjustment signal 130 to a process control unit 132. The process control unit 132 may be any of a variety of devices used to effect a change in the measured physical parameter of the sheet material 10.

The synchronous detectors 74, 76, and 78 are conventional circuits in which a relatively strong, low-noise response may be used to condition relatively weak, high-noise responses by way of providing a reference of the general shape and phase of the latter responses in the absence of high noise. The low-noise response is the reference response 102 that is derived from the response 62 of the phase-reference detector 54.

Figure 2:
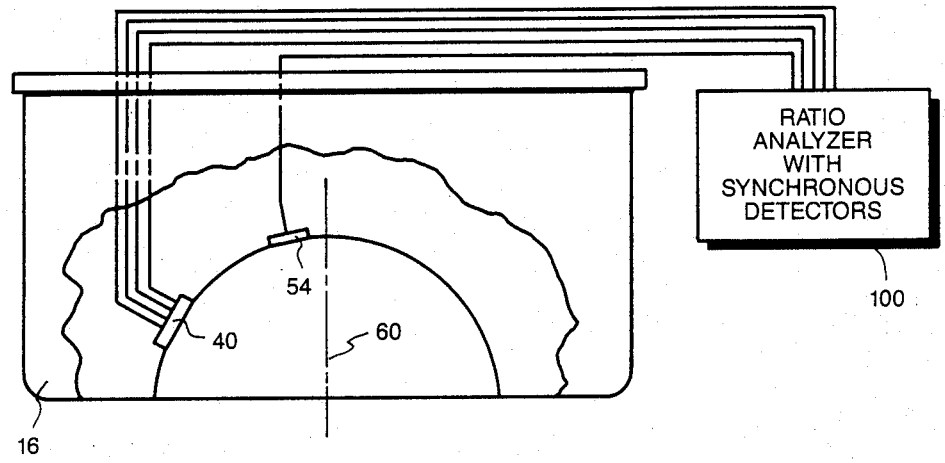
FIG. 2 is a schematic illustration of a further refinement of the invention as applied to the embodiment of FIG. 1.

The phase-reference detector 54 need not be incorporated in the integral package 40, but may be used in isolation therefrom as shown in FIG. 2. In an especially-preferred embodiment, the phase-reference detector 54 is separated from the integral package 40 and located along the transmission axis 60. This maximizes the response 62 of the phase-reference detector 54 while simultaneously allowing displacement of the integral package 40 from the transmission axis 60.

The method of conditioning detector responses in accordance with the response 62 from the phase-reference detector 54 is applicable to prior apparatus and processes which employ a single detector or plural, separate detectors. Especially where the conventional detector or detectors are offset from the source (i.e. displaced from the transmission axis) of radiation, this method offers an effective means for processing weak detector responses having correspondingly low signal-to-noise ratios.

While the invention has been described with reference to preferred embodiments, the description is intended as illustrative and not as restrictive. Those skilled in the art of measuring physical parameters of sheet material via infrared absorption phenomena will recognize that numerous modifications can be made without departing from the spirit and scope of the invention.

What is claimed is:

1. An apparatus containing a source of electromagnetic radiation and being adapted for measurement, via infrared absorption phenomena, of one or more physical parameters of sheet material during production thereof, comprising:
   (a) a sensor housing. and
   (b) an integral filter-detector package contained within the sensor housing and containing both a plurality of separate filters, at least three of which pass selected narrow bands of infrared radiation that is directed from the source and that interacts with the sheet material, and a corresponding plurality of detectors which detect the radiation that passes through the filters.

2. An apparatus as in claim 1 wherein the detectors are disposed on a common substrate.

3. An apparatus as in claim 2 further comprising a thermoelectric cooler that is contained within the integral package.

4. Apparatus as in claim 3 wherein the plurality of filters includes a fourth filter that is selected to pass a band of radiation that is relatively broad in comparison to the narrow bands.

5. Apparatus as in claim 4 wherein the integral package has a location along the transmission axis of the source.

6. An apparatus as in claim 1 wherein the integral package is displaced from the transmission axis of the source.

7. Apparatus as in claim 6 wherein the plurality of filters includes a fourth filter that is selected to pass a band of radiation that is relatively broad in comparison to the narrow bands.

8. An apparatus as in claim 1 further comprising a phase-reference detector separate from the integral package.

9. An apparatus as in claim 8 wherein the phase-reference detector has a location along the transmission axis of the source.

10. A process for measuring physical parameters of sheet material by directing electromagnetic radiation from a source to the material and electronically processed infrared detector responses associated with selected bands of infrared radiation which passes through or otherwise interacts with the material, comprising the steps of:
   (a) filtering the electromagnetic radiation to simultaneously pass at least three different bands of radiation through at least three corresponding filters; and
   (b) detecting the radiation passing through the filters, wherein both the filtering and detecting steps are performed within an integral filter-detector package which is contained within a sensor housing.

11. A process as in claim 10 further comprising the step of internally cooling the integral filter-detector package.

12. An apparatus for measuring physical parameters of sheet material by directing electromagnetic radiation from a source to the material and electronically processing detector responses associated with selected bands of radiation which passes through or otherwise interacts with the material, comprising:
   (a) first means for detecting a relatively broad band of radiation emitted from the source;
   (b) second means for detecting at least two relatively narrow bands of radiation emitted from the source; and
   (c) means for conditioning detector responses from the second means in accordance with a detector response from the first means to produce at least two conditioned responses.

13. An apparatus as in claim 12 wherein the second means comprises a plurality of filters and a corresponding plurality of infrared detectors, all contained within an integral filter-detector package.

14. An apparatus as in claim 13 wherein the detectors of the second means are disposed on a common substrate.

15. An apparatus as in claim 14 further comprising a thermoelectric cooler contained within the integral filter-detector package.

16. An apparatus as in claim 15 wherein the integral filter-detector package is displaced from the transmission axis of the source.

17. An apparatus as in claim 16 wherein the first means has a location along the transmission axis of the source.

18. An apparatus as in claim 16 wherein the integral filter-detector package also contains the first means.

19. An apparatus as in claim 16 further comprising means for processing the conditioned responses to produce at least one measurement response indicative of at least one physical parameter of the sheet material.

20. Apparatus as in claim 15 wherein the integral package has a location along the transmission axis of the source.

21. Apparatus as in claim 20 wherein the integral package also contains the first means.

22. Apparatus as in claim 12 wherein the second means comprises a plurality of at least three filters and a corresponding plurality of infrared detectors , all contained within an integral filter-detector package.

23. A process for measuring physical parameters of sheet material by directing electromagnetic radiation from a source to the material and electronically processing infrared detector responses associated with selected bands of infrared radiation which passes through or otherwise interacts with the material, comprising the steps of:
   (a) filtering the electromagnetic radiation to pass a relatively broad band of radiation;
   (b) detecting the radiation passed in the filtering step to produce a phase-reference detector response;
   (c) simultaneously filtering the electromagnetic raditation to simultaneously pass at least two relatively narrow bands of radiation;
   (d) separately detecting the different bands of radiation passed in the simultaneous filtering step to produce at least two infrared detector responses; and
   (e) conditioning the infrared detector responses in accordance with the phase-reference detector response to produce at least two conditioned responses.

24. A process as in claim 23 wherein both the simultaneous filtering and separate detecting steps are performed within an integral filter-detector package which is contained within a sensor housing.

25. A process as in claim 24 further comprising the step of internally coolin the integral package.

26. A process as in claim 25 further comprising the step of processing the conditioned responses to produce at least one measurement response.

* * * * *